United States Patent
Borck

(10) Patent No.: US 8,486,434 B2
(45) Date of Patent: Jul. 16, 2013

(54) MEDICAL IMPLANT CONTAINING AN ANTIOXIDATIVE SUBSTANCE

(75) Inventor: Alexander Borck, Aurachtal (DE)

(73) Assignee: Biotronik VI Patent AG, Baar (CH)

(*) Notice: Subject to any disclaimer, the term of this patent is extended or adjusted under 35 U.S.C. 154(b) by 178 days.

(21) Appl. No.: 12/839,740

(22) Filed: Jul. 20, 2010

(65) Prior Publication Data

US 2011/0034996 A1 Feb. 10, 2011

Related U.S. Application Data

(60) Provisional application No. 61/231,688, filed on Aug. 6, 2009.

(51) Int. Cl.
*A61F 2/00* (2006.01)
*A61F 2/06* (2006.01)

(52) U.S. Cl.
USPC .......................... 424/423; 424/422; 623/1.15

(58) Field of Classification Search
None
See application file for complete search history.

(56) References Cited

U.S. PATENT DOCUMENTS

| 6,981,985 B2 * | 1/2006 | Brown et al. ................ 623/1.15 |
| 2004/0098108 A1 | 5/2004 | Harder et al. |
| 2009/0081253 A1 * | 3/2009 | Hanon et al. ................ 424/206.1 |
| 2010/0008970 A1 * | 1/2010 | O'Brien et al. ................ 424/426 |

FOREIGN PATENT DOCUMENTS

EP 1 419 793 5/2004

OTHER PUBLICATIONS

Kelly (Alternative Medicine Review 1999, 4(1), 29-36).*

* cited by examiner

*Primary Examiner* — Ernst Arnold
(74) *Attorney, Agent, or Firm* — Greer, Burns & Crain, Ltd.

(57) ABSTRACT

One embodiment of the invention concerns a medical implant having a basic body that includes the antioxidative substance squalene incorporated into at least one of the basic body and a coating on at least a portion of the basic body, the incorporated squalene being present in quantities of 0.4 µg to 2000 µg.

16 Claims, No Drawings

MEDICAL IMPLANT CONTAINING AN ANTIOXIDATIVE SUBSTANCE

CROSS REFERENCE

The present application claims priority on U.S. Provisional Application No. 61/231,688 filed on Aug. 6, 2009.

FIELD

One example embodiment of the invention concerns a medical implant with the basic body having an antioxidative substance.

BACKGROUND

Medical implants have found applications in many embodiments in modern medical technology. They are used, for example, to support vascular structures, hollow organs and endovascular implants for fastening and temporary fixation of tissue implants and tissue transplants, but also for orthopedic purposes, for example, as nails, plates or screws.

Thus, for example, the implantation of stents has established itself as one of the most effective therapeutic measures in the treatment of vascular disease. One of the most frequent causes of death in the developed world is cardiovascular diseases, whereby coronary diseases have the highest significance. For the treatment of these diseases, intravascular stents are used, for example, balloons or stents are inserted into the affected blood vessel of the patient, and if necessary, implanted in order to expand such and keep it open.

The implant or stent has a basic body made of an implant material. An implant material is typically an inorganic material that is used for a medical application and which interacts with biological systems. A basic requirement for a material used as implant material that comes in contact with the body when used as intended, is its biocompatibility. Biocompatability is understood to mean the ability of a material to provoke an appropriate reaction of the tissue in a specific application. This includes the adaptation of the chemical, physical, biological and morphological surface properties of an implant to the recipient tissue with the goal of a clinically desired interaction. The biocompatibility of the implant material is also dependent on the chronological reaction of the biosystem that receives the implant. Thus, irritations and inflammations occur relatively quickly, which could lead to tissue changes. Biological systems react in various ways depending on the properties of the implant material. According to the reaction of the biosystem, the implant materials can be divided into bioactive, bioinert and degradable/resorbable materials.

However, because of the intravascular intervention, increased thrombus formation can take place, as well as increased proliferation of smooth muscle cells, which can lead to a new stenosis, a restenosis. Overshooting proliferation of scar tissue thereby leads to restenosis in approximately 30-40% of all uncoated stents after a longer period of time.

In order to prevent the risk factors of a restenosis, a number of coatings for stents were developed that are intended to offer increased hemo-compatibility. However, these coated implants have the problem that, as a rule, they have a short shelf-life after having been produced up to the implantation time, i.e. they can only be stored for a short time, or they also require storage conditions such as, for example, storage of the products at 4° C. This leads to increased waste of completed products and thus to an increased economic loss as well as increased costs with respect to energy consumption. Particularly medical implants made of polymeric materials or with coatings of polymeric materials, perhaps loaded with active substances, must be improved with respect to their shelf-life and storage stability.

Further, many of these coated stents that are loaded with active substances have the disadvantage that the active substances are released too slowly at the surrounding implantation site, as well as that their bioavailability of the respective coating materials is too low. Further, in the selection of the dosage of the active substances that are to be released, it is limiting, that the quantity of the active substance that is to be placed on the exterior of the stent is severely limited because the surface area that is available for application at the stent is very small. Stents of biocorrodible magnesium alloys can have the additional problem that the strongly alkalinity that is created as a result of the corrosion of the material, negatively influences the resorption behavior of the active substance that is to be absorbed. Thus, active substances are sometimes used as hydrochlorides when the solubility of the active substance is too low. However, in the strongly alkaline environment that is created, such hydrochlorides are again transformed into difficult to dissolve, deprotonized active substances.

One problem in the use of biocorrodible implants that consist entirely or partially of a metallic material is also that the decomposition products that are created in the corrosion process of the implant and released often have a significant influence on the local pH value and can lead to undesired tissue reactions. Moreover, because of their increased rate of corrosion, these implants often have an implant integrity that is too short at the implant site for the desired application. Particularly in the degradation of Mg-containing biocorrodible implant materials, the pH value in the immediate environment can rise. This rise in the pH value can lead to a phenomenon that is summarized by the term alkalosis. The increase in local pH value thereby leads to an imbalance of the load distribution in the smooth muscle cells surrounding the vascular structure, which can have the effect of increasing tonicity in the area of the implant. This increased pressure on the implant can lead to the premature loss of the integrity of the implant. If the implant is, for example, a stent, a restenosis can occur in the course of such a vasoconstriction in the vascular structure around the stent or to an impairment of the vascular lumen.

SUMMARY

In some embodiments of the invention, the shelf-life of the coated medical implants, as well as the bio-availability and resorption of pharmaceutically active substances, is improved when they are a component of the coating of an implant. Further, the resistance to corrosion of biocorrodible, medical implants is improved.

This and other problems are solved by, for example, making a medical implant available, whereby the basic body has at least the one antioxidative substance squalene and the squalene is incorporated in the basic body in quantities 0.4 µg to 2,000 µg and/or is present in a coating of such.

DETAILED DESCRIPTION

The present application claims priority on U.S. Provisional Application No. 61/231,688 filed on Aug. 6, 2009, which is incorporated herein by reference.

Some example embodiments of the invention take advantage of the discovery that an addition of small quantities of squalenes improves absorption by the tissue, as well as the bioavailability of pharmaceutically active substances without disadvantageously influencing the other mechanical properties of the implant. The mechanical properties of some implant materials can even be improved. Moreover, it has been shown that small quantities of squalenes can already significantly improve the shelf-life and storage of medical implants. Additionally, small quantities of squalenes are sufficient in order to notably delay the corrosion of the biocorrodible implant Squalene, also called 2,6,10,15,19,23-hexamethyl-2,6,10, 14,18,22-tetracosahexaene, spinacene or supraene, belongs to the class of isoprenoids and is seen as the backbone of triterpenes (C30) and plays an important role in the biosynthesis of vitally important substances of higher organisms. This symmetrically built aliphatic compound is primarily a starting material for the formation of steroids to which important compounds such as steroles, gallic acid, steroid hormones, vitamins of the D group, saponine and cardiac glycosides belong. In the biosynthesis of, for example, cholesterol, squalene is obtained intermediately by reductive dimerization of farnesyldiphosphate, which subsequently reacts again in a squalene oxide intermediate step into lanostearol, a precursor of cholesterol.

An important advantage of squalene is its significantly improved compatibility with the body with respect to toxicity compared to the other isoprenoids or isoprenoid derivatives, as well as its improved enrichment in the body. Thus, for example, lycopene and ubichinon are already toxic in concentrations of 10 μmol/l. Squalene, on the other hand, is not toxic, even in concentrations of 100 μmol/l.

The use of squalenes as exipient on medical implants includes at least two decisive advantages.

In implants that release active substances, the total quantity of the load of active substances can be reduced without lessening the potency of the implant. The lipophilic properties of squalene are responsible for this. The distribution of active substances or also the penetration of active substances is influenced. The squalene can be applied just like a film on the inside of the vascular structure, the active substance that is dissolved in the squalene film or has immigrated from the implant is thereby fixated longer at the implant site and has more time to get into the desired target tissue. The absorption into the cells is improved and thus the availability is increased. Thereby, it is not critical whether the active substance comes from holes or from cavities in the implant or was released by a polymeric matrix.

In the case of polymeric matrices, the exipient has additional very favorable properties. The addition of squalene makes polymers such as, for example, PLLA, softer and more flexible. As a result of the modification of mechanical properties, the entire implant is improved. This becomes visible on the example of a coronary stent. Polymeric coatings can, when a plastic deformation takes place, chip off or develop cracks (micro cracks). Chips are of particular concern because in this case, the danger of a thrombosis is given.

Cracks in the polymer layer that carries active substances change the release behavior, the release kinetics. As a result, the therapeutic window could be missed or the release of active substance remains unused due to intermittent overdosing.

In addition to the stents that are suitable for longer release periods of active substances at the implant site, a possibility exists of releasing active substances in the short term via balloons. Here, the exipient as described above for the improvement of tissue penetration is suitable, which is due to the lipophilic properties of the molecule. Additionally, by adding squalenes in the lower percentage range, the form of administration can be optimized. Many active substances such as, for example, paclitaxel crystallize on the balloon material. This may have a number of disadvantages, including:

insufficient adhesion of the crystals on the balloon material
loss of active substance as a result of mechanical influences
delay of the dissolution rate By using the exipient squalene, this crystallization can be prevented or inhibited. The active substance exipient mixture can be applied in the form of a paste-like mass, which avoids several disadvantages.

Additionally, the range of applications of squalenes can be optimized. Squalene tends to polymerize by itself when exposed to air. As a result of naturally or artificially induced polymerization of the exipient, the properties of the material can be adapted even better. The polymeric form of the exipient has lower diffusion properties and it remains available longer locally, for example, as a softener.

In the case of implants that carry active substances it could be shown that in spite of accelerated aging, the storage stability is improved. Squalene acts as antioxidant or as radical interceptor. As a result of the addition of the exipient in quantities of less than 1%, the shelf-life of an implant that is loaded with active substance can be extended by, for example, three to six months compared with probes that do not contain the antioxidant; and no decomposition products could be detected using HPLC analytics.

In one embodiment, the medical implant has a basic body, whereby squalenes are incorporated into the basic body in quantities of 0.4 μg to 2000 μg and/or are present in a coating of such. In another embodiment, the medical implant has a basic body, whereby from 4 μg to 400 μg of squalene is incorporated into the body and/or is present in a coating of such. In another embodiment, the medical implant has a basic body into which squalene is incorporated in quantities of 40 μg to 100 μg and or is present in a coating of such.

Within the scope of the present invention, medical implants are any medical device that is used, at least in part, in order to be inserted into the body of a patient. Examples are implantable devices such as pace makers, catheters, needle injection catheters, blood coagulation filters, vascular transplants, balloons, stent transplants, gall bladder stents, intestinal stents, bronchial lung stents, esophageal stents, urinary tract stents, aneurism-filling spools and other spool devices, trans-myocardial re-vascularization devices, percutaneous myocardial revascularization devices. Further, any natural and/or artificial medical products can be used, for example, prostheses, organs, vascular structures, aortas, heart valves, tubes, organ replacement parts, implants, fibers, hollow fibers, membranes, cans, blood containers, titer plates, adsorb media, dialysators, connection pieces, sensors, valves, endoscopes, filters, pump chambers as well as other medical products, which are to have hemocompatible properties. The term medical product is widely conceived and describes particularly such products that come in brief (e.g. endoscopes) or permanent (e.g. stents) contact with the blood.

In some embodiments medical implants are catheters (balloon catheters) and stents. Indeed, some invention implant embodiments in the form of stents or catheters are believe to be of particular utility and benefit due to the novel and valuable features of the invention.

Conventionally designed stents have a filigree support structure made of metallic rods that are at first present in a non-expanded condition for insertion into the body and that then are expanded into an expanded condition at the site of the application. The stent can be coated prior to or subsequent to crimping onto a balloon.

Biocorrodible Basic Implant Bodies

Within the meaning of the present invention, the term biocorrodible (basic) implant (body) preferably means biocorrodible (basic) stent (body), that the basic body decomposes in a physiological environment, particularly in the vascular system of a human or animal organism, i.e. it decomposes in such a way that the stent loses its integrity. In an embodiment, biocorrodible basic bodies degrade only when the functions of the implant no longer make physiological sense or are no longer necessary. For biocorrodible stents, this means that the stent may decompose or lose its integrity only when the traumatized tissue has healed and the stent thus does not need to remain in the vascular lumen any longer.

In one embodiment, the biocorrodible basic body (material) includes a metallic material that is a biocorrodible alloy, whereby the main ingredients of the alloy are selected from the group consisting of magnesium, iron, zinc, manganese and/or wolfram. In one embodiment, the biocorrodible metallic material is a magnesium alloy.

The alloy, particularly comprising magnesium, iron, zinc and/or wolfram is to be selected in its composition in such a way that it is biocorrodible. In an embodiment those alloys are described as being biocorrodible for which, in physiological environments, degradation takes place that in the end leads to a loss of the mechanical integrity of the entire stent or of that part of the stent that is made of the material. In one embodiment, the main component is that component of an alloy that has the largest proportion of weight. The proportion of the main component may be more than 50% by weight. In another embodiment the proportion is more than 70% by weight. Other weight proportions will also be useful. In yet another embodiment, a magnesium alloy is used.

If the material in accordance with the invention is a magnesium alloy, it may contain yttrium and other rare earth metals, as an alloy of this type distinguishes itself by its physicochemical properties and its high biocompatibility, particularly also its degradation products. Other materials may also be included.

In one embodiment, the yttrium (W) and rare earths (E)-containing, biocorrodible magnesium alloys (WE43 & WE54 of magnesium electron) that are described in EP 1 419 793 B1, are used for the manufacture of implants (stents) with a proportion of magnesium >90 by weight, yttrium 3.7-5.5% by weight, rare earth metals 1.5-4.4% by weight and the remainder <1% by weight.

These magnesium alloys have confirmed their suitability in experiments and in clinical trials, i.e. they show a high biocompatibility, favorable processing properties, good mechanical properties and an adequate corrosion behavior for the purposes of use.

In the present embodiment, the collective description "rare earth metals" SE, refers to a number of elements, including the following: scandium (21), yttrium (39), as well as the "light rare earth metals" LSE lanthan (57), cerium (58), neodymium (60) and promethium (61), and the "heavy rare earth metals" SSE samarium (62), europium (63), gadolinium (64), terbium (65), dysprosium (66), holmium (67), erbium (68), thulium (69), ytterbium (70) and lutetium (71).

Basic implant bodies, including basic stent bodies, can comprise or consist of degradable polymers including: polydioxanone; polyglycolide; polycaprolactone; polyhydroxy valeric acid; polyhydroxy butyric acid; polylactides such as poly(l-lactide), poly(d-lactide), poly(d,l-lactide) and blends such as copolymers, poly(l-lactide-co-glycolide), poly(d,l-lactide-co-glycolide), poly(l-lactide-co-d-1-lactide), poly(l-lactide-co-trimethylene carbonate) and tri-block copolymers; polysaccharides such as chitosan, levan, hyaluronic acid, heparin, dextran and cellulose.

Permanent Basic Implant Bodies

In contrast to biocorrodible, degradable basic bodies, the "permanent basic implant body" is not degraded in large part in a physiological environment in a human or animal organisms so that it does not lose its integrity. In one embodiment the "permanent basic implant body" may be a "permanent basic stent body."

In another embodiment, the permanent basic implant body comprises or consists of a form-memory material preferably made of one or several materials such as nickel-titanium alloys and copper-zinc-aluminum alloys, and nitinol.

In another embodiment, the permanent basic implant body includes stainless steel, such as Cr—Ni—Fe steel, the alloy 316L, Co—Cr steel or PERSE, a platinum-enriched stainless steel, or other stainless steel or other iron containing alloy.

In yet another embodiment, the basic implant body includes plastic such as polyurethane and/or ceramics and/or additional polymer coatings.

Within the scope of the present invention, some example catheters are tubules or hoses of various diameters that can be introduced into the body cavity that is to be treated. So-called balloon catheters are used primarily in angioplasty for the expansion and reopening of a vascular structures. A guiding wire is first inserted into the vascular structure that is to be treated and subsequently, the balloon catheter, which consists of a hose that has a non-dilated balloon in a specified section along the hose, is slid along the guiding wire up to the point at which the vascular structure is to be treated so that the balloon is placed at the site of the vascular structure that is to be treated, which has, for example, a stenosis. After that, the balloon is dilated, i.e. unfolded and/or expanded so that the site that is to be treated is reopened or expanded. Finally, the balloon is emptied again and is removed from the vascular structure along the guiding wire. At the same time or subsequently, the guiding wire is also pulled out of the vascular structure. As a result of the expansion or reopening of the vascular structure, the flow of the body fluid in the vessel is no longer impaired or not impaired to the degree of the prior condition. The present invention also includes other example catheters that do not include some or all of these features.

Some balloon catheters in accordance with the invention may consist of a material containing a polymer, a copolymer and/or a mixture of several polymers and/or copolymers. In principle, polymers or copolymers can be used here that have the necessary stability and flexibility for insertion into a catheter. Those knowledgeable in the art will appreciate that there are numerous such polymers and copolymers or mixtures thereof. The compatibility as well as other properties of the polymer can be determined in simple routine experiments or may even be predicted. In one embodiment polymers and/or copolymers that have at least a repeating monomer with at least one amide group are utilized. Particularly polyamides, polyamide copolymers or polyamide-containing copolymers can be used. Thereby, polyamides with at least 6 C atoms per monomer may be used in one example, with more than 10 in another example, and with 12 C atoms in yet another example. In another embodiment polyamide-12 or polyamide-12-copolymers such as polyamide-12/6 can be used. Even polyether block amides (e.g. those under the brand name PEBAX®) can be used. In another example polymers or copolymers of the group of polyesters, co-polyesters and/or polyester elastomers can be used.

This type of balloon catheter can also be used for inserting intra-luminal endoprostheses (stents) into a body cavity at a site that is to be treated.

In an embodiment, squalene is incorporated into the basic implant body in quantities of 0.4 μg to 2,000 μg. This may be used with implants consisting of a material that is selected from the group of biocorrodible and permanent polymers, for example, 4 μg to 400 μg. It has been shown especially, that the polymeric matrix is significantly stabilized by the squalene, and thus a longer shelf-life of these implants can be attained. As a result of the addition of the antioxidative substance squalene, radicals that enter into the polymeric matrix or that are created there can be neutralized immediately.

In another embodiment, the squalene is present in quantities of 40 μg to 100 μg as a coating on the basic body of the medical implant.

A coating may be an application of the components in sections onto the basic body of the implant. In one embodiment, the entire surface of the basic body of the implant, particularly a stent or a balloon catheter, is covered by the coating. The thickness of the layer may be in the range of 1 μm to 100 μm, particularly 3 μm to 15 μm. The coating may consist of the antioxidative substance squalene.

In a further embodiment, the coating contains at least one antioxidative substance such as one or more pharmaceutically active substances. The squalene may be present in quantities of 1% to 2% as coating on the basic body of a medical implant.

In an alternative embodiment, the coating, including the at least one antioxidative substance squalene, can be present as a cavity filling or as a component of the filling of a cavity. The implant, particularly the stent, has one or several cavities for this purpose. The cavities are, for example, on the surface of the implant and can be created, for example, by laser ablation in nano to micro meter dimensions. In implants, particularly stents with a biodegradable basic body, a cavity can also be located in the interior of the basic body, so that the release of the material occurs only after exposure. In this embodiment, the cavity is enclosed in the body interior so that it and its contents are isolated from the external environment until some portion of the basic body has decomposed to expose the interior cavity and the material contained therein. In this manner, release of the internally contained material can be delayed through the period of time required to decay a portion of the basic body to expose the cavity. The term "cavity" thereby comprises, for example, holes or recesses that are open to the environment (with an example being a concave indentation in a surface) in addition to an interior cavity that is not open to the environment.

In addition to the antioxidative substance, the coating can have one or more pharmaceutically active substances. Alternatively, the named substances can be components of the filling of a cavity.

A pharmaceutically active substance within the scope of the present invention may be a substance (active substance) selected from the group including antiphlogistics, for example dexamethasone, methylprednisolone and diclophenac; cytostatics, including paclitaxel, colchicines, actinomycine D and methotrexate; immunosuppressivs, including limus compounds, further preferred sirolimus (rapamycine), zotarolimus (Abt-578), tacrolimus (FK-506), everolimus, biolimus, especially biolimus A9 and pimecrolimus, cyclosporin A and mycophenolic acid; thrombocyte aggregation blockers, including abciximab and iloprost; statins, including simvastatin, mevastatin, atorvastatin, lovastatin, pitavastatin, pravastatin and fluvastatin; estrogens, including 17b-estradiol, daizeins and genisteins; lipid regulators, including fibrates; immunosuppressive drugs; vasodilatators, including sartane; calcium channel blockers; calcineurine inhibitors, including tacrolimus; anti-inflammatory drugs, including imidazole; antiallergic drugs; oligonucleotides, including decoyoligodesoxynucleotide (dODN); endothelial bilders, preferable fibrin; steroids; proteins/peptides; proliferation blockers; analgetics and antirheumatics; endothelial receptor-antagonists, including bosentan; rho-kinase inhibitors, including fasudil; RGD-peptides and cyclical RGD (cRGD) (comprising the sequence Arg-Gly-Asp); and organic gold compounds or platinum compounds. Other pharmaceutically active materials are also useful in invention embodiments.

The pharmaceutically active substance may be contained in a pharmaceutically active concentration of 0.2 to 3.5 pμg/mm² on the stent surface, more preferred 0.25 to 1.45 μg/mm² on the stent surface.

Thereby, the coating contains the quantity of squalenes specified above. As a result of the antioxidative effect, the pharmaceutically active substances that would otherwise be subject to degradation are preserved in the matrix. This degradation is the reason why conventional implants that release active substances are provided with a relatively short shelf-life of six months up to one year. The antioxidative effect increases shelf-life by, for example, three to six months. This represents an important and valuable advantage over the prior art.

As a result of the improvement of the mechanical properties, such as less brittleness, cracks and chipping is lessened, and as a result there is no excessive release of active substances, which must be compensated by higher loads, respectively overcompensated by such. Still further advantages are thereby achieved.

The permeability of the active substance is increased by the very highly lipophilic substance squalene, which additionally contributes to the savings or reduction of the load of the pharmaceutically active substance on the implant without thereby reducing the effectiveness. This achieves still further advantages and benefits.

The coating can consist of an antioxidative substance and perhaps one or more pharmaceutically active substances that absorb a biostable and/or biodegradable polymer matrix. Alternatively, the identified substances can be a component of a cavity filling. The antioxidative and the pharmaceutically active substances can be present spatially separate from each other in the coating, perhaps also in different matrices.

A biostable and/or biodegradable polymer matrix or polymer layer within the scope of the invention may be an application, at least in sections, of the components in the coating on the medial implant. In one embodiment, the entire surface of the medical implant is covered by the coating. The thickness of the layer may be in the range of 2 μm to 60 μm, for example 10 μm to 30 μm. Other thicknesses may also be useful, with examples including those greater than 60 μm and thinner than 2 μm.

The coating can be applied directly onto the medical implant. The processing can be performed according to standard procedures for coating. Single-layer, but also multi-layer systems (for example, so-called base coat, drug coat or top coat layers) can be created. The coating can be applied directly to the basic body of the implant or additional layers could be provided in between, that are, for example, designed to provide adhesion.

The biostable and/or biodegradable polymer layer within the scope of some embodiments of the present invention may be composed of polymers including non-resorbable, permanent polymers and/or resorbable, biodegradable polymers.

In one embodiment the biostable and/or biodegradable polymer layer is composed of polymers selected from the group of polyolefins, polyether ketones, polyether, polyvinyl alcohols, polyvinyl halogenides, polyvinyl esters, polyacrylates, polyhalogene olefins, polyamide, polyamide imides, polysulfones, Polyesters, Polyurethanes, silicone, polyphosphazenes, polyphenylenes, polymer foams (of styroles and carbonates), polydioxanones, polyglycolides, polylactides, poly-ε-caprolactone, ethylvinyl acetate, polyethylene oxide, polyphosphoryl choline, polyhydroxy butyric acids, lipids, polysaccharides, proteins, polypeptides as well as copolymers, blends and derivates of these compounds.

In other embodiments, the biostable and/or biodegradable polymer coating is composed of polymers selected from the group consisting of polypropylenes, polyethylenes, polyisobutylenes, polybutylenes, polyetherether ketone, polyethylen glycol, polypropylene glycol, polyvinyl alcohols, polyvinyl chloride, polyvinyl fluoride, polyvinyl acetate, Polyethylacrylate, polymethyl acrylate, polytetrafluoro ethylene, polychlortrifluoro ethylene, PA 11, PA 12, PA 46, PA 66, polyamide imide, polyethersulfone, polyphenylsulfone, polycarbonate, polybutylene terephthalate, polyethylene terephthalate, elastane, pellethane, silicone, polyphosphazene, polyphenylene, polymer foams (of styrols and carbonates), polydioxanone, polyglycolide, poly-l-lactide, poly-d-lactide, and poly-d,l-lactide, as well as poly-ε-caprolactone, ethylvinyl acetate, polyethylene oxide, polyphosphoryl choline, polyhydroxy valerate, cholesterol, cholesterol ester, alginate, chitosan, levan, hyaluronic acid, uronide, heparin, dextran, cellulose, fibrin, albumin, polypeptide and copolymers, blends and derivates of these compounds.

In another embodiment, the biostable and/or biodegradable polymer layer is based upon the desired rate of elution, as well as the individual properties of the various active substances that are used and on the various rates of resorption or degradation at the site of action of the medical product.

EXAMPLE OF EMBODIMENT 1

Stent Coated with Squalenes that Releases Active Substances

A permanent, or optionally, a biocorrodible sent is coated as follows:

The stent is cleaned of dust and residuals and clamped into a suitable stent coating apparatus (DES Coater, developed by the company Biotronik). With the aid of an airbrush system, the rotating stent is coated on one side under constant ambient conditions (room temperature; 42% humidity) with PLLA, containing pharmacologically active substance and squalene as exipient (up to 2% based on the proportion of solid substances of the coating solution). At a nozzle distance of 20 mm, a stent that is 18 mm long is coated after approximately 2 minutes. After the intended mass of the layer has been reached, the stent is dried for approximately 5 minutes at room temperature before being turned around and again clamped in for coating the uncoated side in the same way.

EXAMPLE OF AN EMBODIMENT 2

Stent Coated with Polymerized Squalenes that Releases Active Substances

Deviating from example of an embodiment 1, the spraying solution contains (10 g PLLA; L210 Boehringer Ingelheim 2.5 l chloroform) the following additional components:
1 ml squalene (density 0.86 g/cm$^3$)
50 µl triethanol amine
5 µl of a vinylpyrrolidon solution containing 0.3% eosin Y Prior to the coating, the components are mixed and stirred in the specified container in the dark.

The stent is coated as described in example of an embodiment 1, in the process the stent is irradiated with a 360 nm UV tube. With the aid of the photo initiator, the cross-linking of the squalene takes place directly at the stent. After 2 minutes, the stent can be rotated and coated on the other side in an analogous way.

It will be apparent to those skilled in the art that numerous modifications and variations of the described examples and embodiments are possible in light of the above teaching. The disclosed examples and embodiments are presented for purposes of illustration only. Many alternatives, equivalents, and variations of elements are possible. Therefore, it is the intent to cover all such modifications and alternate embodiments as may come within the true scope of this invention.

What is claimed is:

1. An implant having a basic body and comprising squalene, wherein the squalene is polymerized with at least one polymer in at least one of the basic body and a polymeric coating, and the squalene is present in quantities of 0.4 µg to 2000 µg.

2. An implant according to claim 1, characterized by, that the squalene is present in quantities of 4 µg to 400 µg.

3. An implant according to claim 1, characterized by, that the squalene is present in quantities of 40 µg to 100 µg.

4. An implant according to claim 1, characterized by, that the implant is a vascular implant.

5. An implant according to claim 4, characterized by, that the implant is provided with one of a biocorrodible or permanent basic body.

6. An implant according to claim 5, characterized by, that the biocorrodible basic body comprises a biocorrodible metallic active substance comprising alloys of the group of magnesium, iron, zinc, manganese or wolfram.

7. An implant according to claim 1, characterized by, that in addition, the implant further comprises at least one pharmaceutically active substance.

8. An implant according to claim 1, wherein the basic body is biocorrodible and consists of an alloy of the group of magnesium, iron, zinc, manganese or wolfram.

9. An implant according to claim 1 wherein:
the squalene is polymerized with at least one polymer in the polymeric coating deposited on at least a portion of the basic body that has a thickness of between about 1 µm and about 100 µm;
the polymerized sqaulene is present in an amount of between about 40 to about 100 µg; and,
the basic body comprises a magnesium alloy.

10. An implant according to claim 1 wherein:
the squalene is polymerized with at least one polymer in the polymeric coating and wherein the squalene is present in a concentration of between about 1% to 2% (wt) in a the polymeric coating deposited on at least a portion of the basic body having a thickness of between about 3 µm and about 15 µm; and
the basic body comprises an alloy that includes yttrium and at least about 70% (wt) magnesium.

11. The implant of claim 1, wherein the polymeric coating comprises poly-L-lactic acid (PLLA) and wherein the squalene is cross-linked with PLLA.

12. The implant of claim 1, wherein the squalene is cross-linked.

13. The implant of claim 1, wherein the squalene is incorporated into the basic body.

14. The implant of claim 13, wherein the basic body is biostable wherein it does not dissolve in a physiologic environment and the squalene is not released into the physiologic environment.

15. A medical implant comprising:
- a biocorrodible basic body;
- a biodegradable polymeric coating covering at least a portion of the basic body, including squalene, wherein the squalene is polymerized with at least one polymer in the coating in an amount of between about 0.4 μg to 2000 μg; and
- a pharmaceutically active material in a concentration of between about 0.2 to 3.5μg/mm$^2$, the coating having a thickness of between about 3 μm and about 15 μm.

16. An implant according to claim 15 wherein the implant is a vascular implant, and wherein the basic body is made of an alloy that includes yttrium, a rare earth metal, and at least about 50% (wt) magnesium.

\* \* \* \* \*